(12) United States Patent
Ripoll et al.

(10) Patent No.: US 9,920,103 B2
(45) Date of Patent: Mar. 20, 2018

(54) PREPARATION OF RECOMBINANT HUMAN PLASMA PHOSPHOLIPID TRANSFER PROTEIN (PLTP) FROM THE MILK OF TRANSGENIC RABBITS

(75) Inventors: Pierre-Jean Ripoll, Mennecy (FR); Laurent Lagrost, Dijon (FR)

(73) Assignees: BIOPROTEIN TECHNOLOGIES SA, Lyons (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 0 days.

(21) Appl. No.: 13/639,969

(22) PCT Filed: Apr. 6, 2011

(86) PCT No.: PCT/IB2011/051482
§ 371 (c)(1),
(2), (4) Date: Jan. 7, 2013

(87) PCT Pub. No.: WO2011/125034
PCT Pub. Date: Oct. 13, 2011

(65) Prior Publication Data
US 2013/0203648 A1     Aug. 8, 2013

(30) Foreign Application Priority Data
Apr. 9, 2010 (FR) ...................................... 10 01490

(51) Int. Cl.
*A01K 67/027* (2006.01)
*C07K 14/47* (2006.01)
*C12N 15/85* (2006.01)

(52) U.S. Cl.
CPC .......... *C07K 14/47* (2013.01); *A01K 67/0275* (2013.01); *A01K 67/0278* (2013.01); *C12N 15/8509* (2013.01); *A01K 2217/052* (2013.01); *A01K 2217/206* (2013.01); *A01K 2227/107* (2013.01); *A01K 2267/01* (2013.01); *C12N 2830/008* (2013.01)

(58) Field of Classification Search
CPC .......... A01K 67/0278; A01K 2217/206; A01K 2227/107; A01K 2217/052; A01K 2267/01; A01K 67/0275; C07K 14/47; C12N 2830/008; C12N 15/8509
See application file for complete search history.

(56) References Cited

U.S. PATENT DOCUMENTS 5,622,843 A *  4/1997  Day et al. .................... 435/69.6
5,831,141 A * 11/1998  Lubon et al. .................... 800/7
6,268,487 B1 *  7/2001  Kutzko et al. ................ 530/414

FOREIGN PATENT DOCUMENTS

WO           95/34289      12/1995
WO           97/42835      11/1997
WO    WO 2003057720 A3 *  3/2004

OTHER PUBLICATIONS

Tollefson et al. "Isolation and characterization of a phospholipid transfer protein (LTP-II) from human plasma." Journal of Lipid Research vol. 29, 1988 , pp. 1593-1602.*
Lagrost L. "Transgenic rabbits to study atherosclerosis."Abstracts of 2nd International meeting on rabbit technology, France. Jun. 2007. pp. 57-58.*
Lwoff et al. "The Concept of Virus."J . General Microbiol (1957) 17: pp. 239-253.*
Prentice et al. "Evolutionary and environmental influences on human lactation." Proceedings of the Nutrition Society (1995), 54, 391400.*
Archer et al. "Human growth hormone (hGH) secretion in milk of goats after direct transfer of the hGH gene into the mammary gland by using replication-defective retrovirus vectors."Proc. Natl. Acad. Sci. USA (1994), 91: pp. 6840-6844.*
Guo, Secretion of Phospholipid Transfer Protein by Human Hepatoma Cell Line, Hep G2, is Enhanced by Sodium Butyrate, Journal of Nutrition, 129, pp. 1984-1991, 1999.
Echelard, Production of Recombinant Therapeutic Proteins in the Milk of Transgenic Animals, BioPharm International, 19, pp. 36-46, 2006.
Houdebine, Production of Pharmaceutical Proteins by Transgenic Animals, Comparative Immunology, Microbiology & Infectious Diseases, 32, pp. 107-121, 2009.
Fan, Transgenic Rabbits as Therapeutic Protein Bioreactors and Human Disease Models, Pharmacology & Therapeutics, 99, pp. 261-282, 2003.
Haperen, Human Plasma Phospholipid Transfer Protein Increase the Antiatherogenic Potential of High Density Lipoproteins Transgenic Mice, Arteriosclerosis, Thrombosis, and Vascular Biology, 20, pp. 1082-1088, 1999.
Keefer, Production of Bioproducts Through the Use of Transgenic Animal Models, Animal Reproduction Science, 82, pp. 5-12, 2004.
Dimond, Transgenic Technology in the Production of Therapeutic Proteins, Innovations in Pharmaceutical Technology, pp. 92-97, 2000.

* cited by examiner

*Primary Examiner* — Titilayo Moloye
(74) *Attorney, Agent, or Firm* — Morgan, Lewis & Bockius LLP

(57) ABSTRACT

The invention relates to obtaining a preparation of recombinant human PLTP from the milk of a transgenic animal containing in its genome one or more copies of a transgene comprising a polynucleotide coding for human PTLP, placed under transcriptional control of a promoter permitting its specific expression in the cells of the mammary glands of said animal. The recombinant human PLTP preparation obtained can be used in the prevention or treatment of septic shock.

4 Claims, 13 Drawing Sheets

Figure 1:
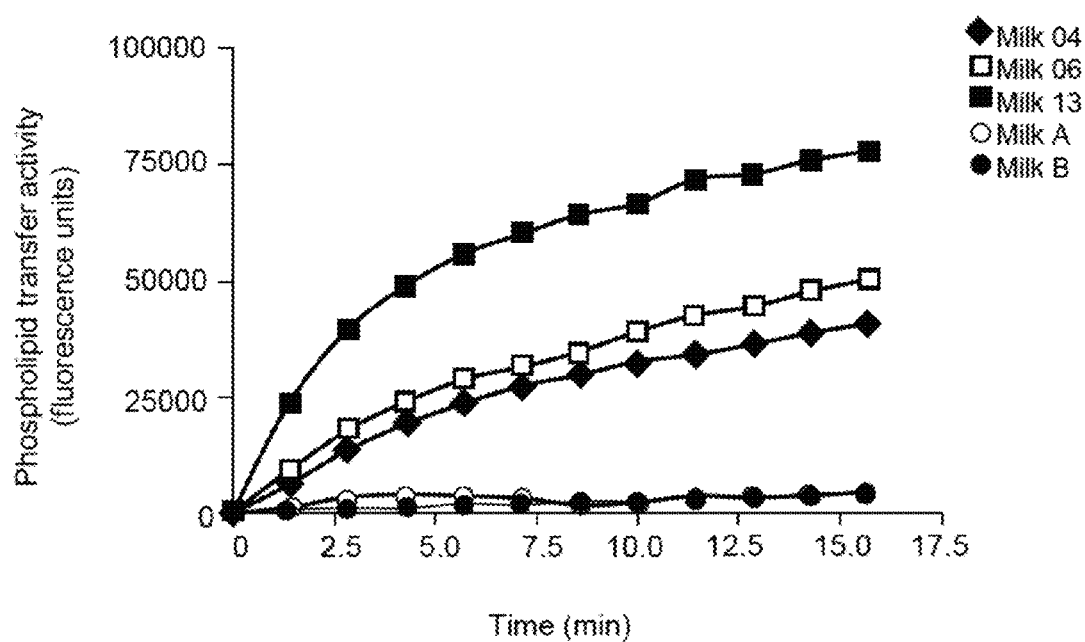

PREPARATION OF RECOMBINANT HUMAN PLASMA PHOSPHOLIPID TRANSFER PROTEIN (PLTP) FROM THE MILK OF TRANSGENIC RABBITS

The subject of the present invention is the preparation of a recombinant human plasma phospholipid transfer protein (PLTP) from milk from transgenic animals, and its uses.

Plasma phospholipid transfer protein (PLTP) was originally identified for its capacity to exchange phospholipids between circulating lipoproteins and to modify the structure and the composition of pro- or antiatherogenic lipoproteins. It belongs to the lipid transfer/lipopolysaccharide binding protein (LT/LBP) gene family which also comprises cholesteryl ester transfer protein (CETP), lipopolysaccharide binding protein (LBP) and bactericidal permeability increasing protein (BPI).

The cDNA for human PLTP, which has been isolated from endothelial cells, has a length of 1750 bp, and contains an open reading frame of 1518 bp, encoding a mature protein of 476 amino acids, preceded by a signal sequence of 17 amino acids; the sequence of the mature PLTP contains, in addition to numerous potential O-glycosylation sites, 6 potential N-glycosylation sites at amino acids 47, 77, 100, 126, 228 and 381 (DAY et al., J Biol Chem, 269, 9388-91, 1994). It has been shown that PLTP effectively bears complex N-glycan structures and that N-glycosylation plays an essential role in the secretion of the protein and also participates in its biological activity (HUUSKONEN & EHNHOLM, Curr Opin Lipidol, 11, 285-9, 2000; QU et al., Protein J, 25, 167-73, 2006).

It has been shown that PLTP exists in the plasma in 2 forms, one that is active and another that is inactive (OKA et al., J Lipid Res, 41, 1651-7, 2000), associated with 2 different types of lipoprotein particles. The active form is associated with particles having an average molecular weight of 160 kDa, close to that of HDLs (high density lipoproteins) while the inactive form is associated with particles having an average molecular weight of 520 kDa, intermediate between that of HDLs and LDLs (low density lipoproteins). KARKKAINEN et al. (J Biol Chem, 277, 15413-8, 2002) describe the separation of these 2 forms from plasma, and report that the active form is associated with apolipoprotein E, and the inactive form with apolipoprotein A-I. Other authors report on the contrary that in plasma, the active form is mainly associated with apolipoprotein A-I, and the inactive form with apolipoprotein E (CHEUNG & ALBERS, J Lipid Res, 47, 1315-21, 2006).

In addition to its phospholipid transfer activity, PLTP also allows the transfer of other amphiphilic molecules, in particular bacterial lipopolysaccharides (LPS), to serum lipoproteins. Experiments in vitro have shown that recombinant PLTP expressed in supernatants of cell cultures could transfer LPSs from the walls of Gram-negative bacteria to HDL particles, and neutralize the biological effects of these LPSs by preventing their binding to the receptors of the cell membranes, in particular CD14 and TLR4 (HAILMAN et al., J Biol Chem, 271, 12172-8, 1996) (VESY et al., Infect Immun, 68, 2410-7, 2000).

This property of PLTP is of most particular interest because bacterial LPSs have very potent pro-inflammatory effects. Their interaction with cell receptors induces the production of pro-inflammatory cytokines, and the triggering of a very strong inflammatory response the most serious manifestation of which, endotoxin shock, or septic shock, can cause death. It has been suggested, on the basis of the LPS transfer and neutralization properties observed in vitro, that PLTP could be used for the treatment of septic shock (U.S. Pat. No. 5,932,536).

The role played by PLTP in neutralizing the effects induced by LPSs has been indirectly confirmed in vivo, in knock-out mice for the PLTP gene, and therefore not expressing this protein (PLTP-KO mice). It has been observed that in these animals, after a single injection of LPS, the association of LPSs with circulating lipoproteins was delayed, the production of inflammatory cytokines (IFN-gamma, IL-6, TNF-alpha) increased and the length of survival was shorter than in the wild-type mice (GAUTIER et al., J Biol Chem, 283, 18702-10, 2008).

However, the biological properties of PLTP and its potential therapeutic uses could up until now not be verified by experiments for administration of PLTP in vivo because no PLTP preparation that could be used in this context was available.

Initially, PLTP was purified from human plasma (DAY et al., J Biol Chem, 269, 9388-91, 1994; TOLLEFSON et al., J Lipid Res, 29, 1593-602, 1988; LAGROST et al., J Lipid Res, 35, 825-35, 1994). However, plasma is relatively low in PLTP (of the order of 50 micrograms of PLTP per gram of total plasma proteins), and also being a complex medium, the purification of PLTP from this medium requires a succession of chromatographic steps that are cumbersome to carry out and which result in a very low purification yield (of the order of 1%). In addition, the activity of plasma PLTP may vary according to its association with plasma lipoproteins and it generally appears, after purification, in the form of several distinct bands the nature and activity of which remain uncertain.

Several attempts have been carried out to produce recombinant PLTP from different mammalian species in various types of transfected eukaryotic cells: BHK cells were used for the production of human or murine PLTP (ALBERS et al., Biochim Biophys Acta, 1258, 27-34, 1995); COS-1 cells for the production of porcine PLTP (PUSSINEN et al., J. Lipid Res., 38, 1473-81, 1997); insect Sf-9 cells infected with a baculovirus (HUUSKONEN et al., Biochim Biophys Acta, 1391, 181-92, 1998); HeLa cells (HUUSKONEN et al., J. Lipid Res., 39, 2021-30, 1998). These expression systems led to the production of proteins of varying molecular weight, often appearing in the form of multiple bands. It has been proposed, in order to produce recombinant PLTP which is as close as possible to plasma PLTP, to use hepatocyte cells HepG2, which are already commonly used for studying the secretion of various lipoproteins and apolipoproteins; indeed, it was assumed that the predominant part of plasma PLTP being produced by the liver, these cells could provide an optimum cellular environment for reproducing the characteristics of native PLTP (GUO et al., J Nutr, 129, 1984-91, 1999). Indeed, the use of this expression system made it possible to obtain a recombinant PLTP having similar characteristics to those of the native protein; the purification of this recombinant PLTP then showed that it was associated with the apolipoprotein E produced by HepG2 cells, in particles of lipoproteins of 160 kDa, resembling the active form of the plasma PLTP previously described by OKA et al. and KARKKAINEN et al. (2000, 2002, previously cited).

However, this expression system, like those previously described, does not allow the production of sufficient quantities of PLTP to allow testing of its activity in vivo, let alone using it for therapeutic purposes.

It is therefore desirable to have available a source of recombinant PLTP which makes it possible to produce this protein in active form and in a sufficient quantity to envisage its effective use.

An alternative to the production of proteins of therapeutic interest by cultures of transformed cells is their production by transgenic animals and in particular in the milk thereof (HOUDEBINE, "*Production of pharmaceutical proteins by transgenic animals. Comparative Immunology*", Microbiology & Infectious Diseases, 32: 107-121, 2009). This approach has theoretically many advantages, and in particular a higher yield, a lower production cost than production in cell cultures, and easier and more flexible scaling up of the production at the industrial level. However, although the possibility of producing in the milk of transgenic mice a recombinant protein, plasminogen inhibitor (tPA), having biological properties similar to those of the native human protein was demonstrated many years ago (GORDON et al., Bio Technol, 5, 1183-7, 1987), the number of proteins that it has been possible to successfully produce in the milk of transgenic animals still remains relatively limited. Indeed, many factors, depending in particular on the nature of the protein of interest to be expressed, can determine success or failure.

Among these factors is in particular the capacity of the host to produce, in the mammary glands, proteins exhibiting post-translational modifications similar to those of the native human protein. This factor is particularly critical if it is envisaged to produce in recombinant form, in milk, proteins such as PLTP, having numerous and varied post-translational modifications (cleavage of the signal peptide and of the propeptide, O-glycosylation and N-glycosylation), and which are naturally produced in the liver. Indeed, the mammary gland cells have the capacity for post-translational modifications different from those of hepatic cells.

It has for example been observed, in the case of coagulation factors, which are part of the proteins whose production in the milk of transgenic animals has been studied the most, that transgenic mice expressing human protein C in their mammary glands could not properly carry out the cleavage of the propeptide and γ-carboxylation (DROHAN et al., Transgenic Res., 355-64, 1994). Similar observations have been made in transgenic pigs, for protein C and for factor IX (LEE et al., J. Biochem., 118, 81-7, 1995; VAN COTT et al., Genet Anal., 15, 155-60, 1999).

Another important factor is the environment that milk constitutes. It is a complex heterogeneous medium that is very rich in proteins and lipids: it is in the form of an emulsion of fat globules in a liquid which is itself a colloidal suspension of casein micelles in an aqueous phase, whey.

Whey notably contains lactose, mineral salts, as well as vitamins and water-soluble proteins. Casein micelles are supramolecular structures consisting of various types of casein (alpha, beta, kappa) which are phosphorylated in varying degrees and associated with calcium via phosphate groups. The majority of the lipids are dispersed in the milk in the form of spherical globules coated with a lipoprotein membrane (DANTHINE et al., Lait, 80, 209-22, 2000), the "milk fat globule membrane" (MFGM), which is a complex assembly mainly consisting of various proteins (MATHER, J. Dairy Sci., 83, 203-47, 2000), associated with phospholipids and neutral lipids.

Given the highly lipophilic nature of PLTP and its capacity to bind cholesterol, phospholipids and diacylglycerides, it could be assumed that if it is produced in milk in recombinant form, it will preferably associate with the fat globule membranes. Insofar as it is moreover known that the activity of PLTP depends on the type of lipoprotein structure with which it is associated, the effects of an interaction between PLTP and the milk fat globules appear difficult to predict.

Moreover, the purification of a recombinant protein of interest produced in the milk of a transgenic animal conventionally starts with a step of clarifying the milk, intended to remove the casein micelles (for example by precipitation at acidic pH, followed by centrifugation), and the fat globules (for example by centrifugation). The protein of interest is then purified from the whey. This approach is generally effective in the case of hydrophilic proteins. However, if the protein is captured by the casein micelles or by the fat globules, its purification may require the use of much more drastic methods with the risk of being harmful to its biological activity.

And yet, the Inventors have now found that, surprisingly, transgenic rabbits expressing, in their mammary glands, a sequence encoding human PLTP produce an active recombinant PLTP in their milk, and that in addition, this PLTP could be extracted from whey.

Consequently, the subject of the present invention is a transgenic animal expressing active human PLTP in its milk. Preferably, said animal is a rabbit.

A transgenic animal in accordance with the invention contains in its genome one or more copies of a transgene comprising a polynucleotide encoding the human PLTP, placed under transcriptional control of a promoter allowing its specific expression in the cells of the mammary glands of said animal.

The expression "transgene" is understood to mean a nucleic acid construct stably inserted into the genome of a host organism, which is transmitted to its progeny from generation to generation. In the present case, the transgene allows the expression of a protein of interest (PLTP) in the milk of the transgenic host animal.

The promoter used to express PLTP may be an endogenous promoter of a gene expressed in the mammary glands of the host organism, or an exogenous promoter. Promoters allowing specific expression in the cells of the mammary gland are known per se. They may be, for example, promoters for casein genes or milk serum proteins: mention may be made in particular of α-, β- or κ-casein promoters, the β-lactoglobin promoter, the α-lactalbumin promoter, the WAP (Whey Acidic Protein) promoter, or the lactoferrin promoter. A preferred promoter is that for WAP, described in patent EP 0 527 063. It is possible to use advantageously an optimized DNA sequence for expression in the mammary glands of the host animal used. Such a sequence may be obtained in silico by techniques well known to a person skilled in the art, in order to remove the cryptic splicing sites, the sequences high in A/T, which destabilize the mRNAs, the polyadenylation sites as well as the potentially parasitic TATA boxes, and the CpG islands, and to optimize the codons in order to reflect the preferences of the cells of the mammary gland of the host animal to produce the milk proteins.

Advantageously, the transgene additionally contains other elements intended to optimize the transcription and/or the translation of the recombinant protein. Such elements are known per se to a person skilled in the art (cf. for example HOUDEBINE, "*Design of expression cassettes for the generation of transgenic animals (including insulators)*", Rat Genomics: Methods in Molecular Biology, Vol 597: 55-69, 2009).

They may be in particular:

- a strong insulator, placed in 5' of the promoter, ensuring a protein expression level that is partly dependent on the number of integrated copies of transgene and that is less dependent on the site of integration of the transgene into the genome of the animal: mention may be made, for example, of the 5'HS4 region of the chicken beta-globin gene (TABOIT-DAMERON et al., Transgenic. Res., 8: 223-235, 1999; RIVAL-GERVIER et al., Transgenic. Res., 12: 723-730, 2003).
- one or more exon/intron pairs which may contain one or more transcription or translation enhancers: by way of example, there may be mentioned: the introns of the late and early genes of the genome of the SV40 virus, the second intron of a beta-globin gene, the introns of the EF1 alpha gene, the introns of the alpha-s1 casein gene, the introns of the WAP gene, the introns of the human and bovine growth hormone genes; the "enhancer" sequences may in particular be chosen from those present in the LTR sequences of the HTLV virus, or of the MMTV virus (murine mammary tumor virus), the "enhancer" sequence of the immunoglobin gene, the "enhancer" sequence of the alpha s-1 casein gene, the "enhancer" sequence of beta-globin. The "enhancer" sequence may also be the distal region upstream (up to 140 kbp) of the WAP gene or the distal region downstream (at least 10 kbp) of the WAP gene, as they are described by RIVAL-GERVIER et al. (Mol. Reprod. Develop., 63: 161-167, 2002), or in the application EP 1 217 071.
- a strong terminator ensuring efficient termination of transcription: by way of example, mention may be made of the SV40 virus early or late gene terminators, those of the beta-globin genes, the WAP genes, the human or bovine growth hormone genes.

Transgenesis may be carried out by conventional methods known per se. Advantageously, the gene construct is introduced by microinjection into one of the pronuclei of fertilized embryos which are then reimplanted into surrogate females. The production of transgenic animals is also possible by nuclear transfer cloning followed by embryo transfer into surrogate females; or by ICSI (Intra Cytoplasmic Sperm Injection), the sperm being incubated in the presence of a transgene, and then introduced into an oocyte; or alternatively by chimerization of embryos from genetically modified cells in vitro, which is used in particular in rats and in mice.

The subject of the present invention is also the milk produced by the transgenic animals in accordance with the invention, and the use of this milk as raw material for the preparation of recombinant human PLTP.

The subject of the present invention is also a method for producing a recombinant human PLTP preparation from the milk of a transgenic animal in accordance with the invention, characterized in that it comprises clarifying the milk, and recovering the whey.

The milk may be clarified by conventional methods known per se to a person skilled in the art. Mention may be made in particular of precipitation of caseins at acidic pH (less than or equal to 4.6), optionally in the presence of a chelating agent, followed by centrifugation in order to remove, on the one hand, the fat globules, and, on the other hand, the casein precipitate. The milk may also be clarified by ultracentrifugation or by tangential filtration.

The whey thus recovered constitutes a recombinant PLTP preparation, and may be used as it is, optionally after concentration, in some applications.

However, it will be generally preferable to carry out an additional step of extracting the PLTP from this whey, which makes it possible to obtain a preparation enriched with PLTP.

Advantageously, this extraction of the PLTP from the whey is carried out by affinity chromatography on heparin attached to an appropriate solid support.

The affinity chromatography on heparin is carried out in a conventional manner by loading the whey onto a column of heparin attached to an appropriate solid support, by carrying out the elution at increasing ionic strength, and by recovering the fractions containing the phospholipid transfer activity.

Generally, the chromatography will be carried out at physiological pH, that is generally at a pH of about 7.4, in the presence of increasing concentrations of NaCl, from 0 to 1 mM. The fractions containing the phospholipid transfer activity are eluted in an NaCl concentration range of 250 to 450 mM, preferably from 300 to 400 mM.

The subject of the present invention is also a preparation of recombinant human PLTP capable of being obtained by the method in accordance with the invention.

This preparation may be used in all the applications proposed for human PLTP, and in particular for the prevention or treatment of septic shock.

Advantageously, this preparation is formulated in the form of a composition capable of being administered by the parenteral route, preferably by injection.

The present invention will be better understood with the aid of the additional description which follows, which refers to non-limiting examples illustrating the production of recombinant human PLTP from the milk of transgenic rabbits, and its efficacy in the treatment of septic shock.

LEGEND TO THE FIGURES

FIG. 1: Comparison of the phospholipid transfer activities in the milks of rabbits WT (Milk A and Milk B) and PLTPTg$_{WAP}$ (Milk 04, Milk 06 and Milk 13). On the x-axis: time in minutes; on the y-axis: phospholipid transfer activity (in fluorescence units).

Figure 2:
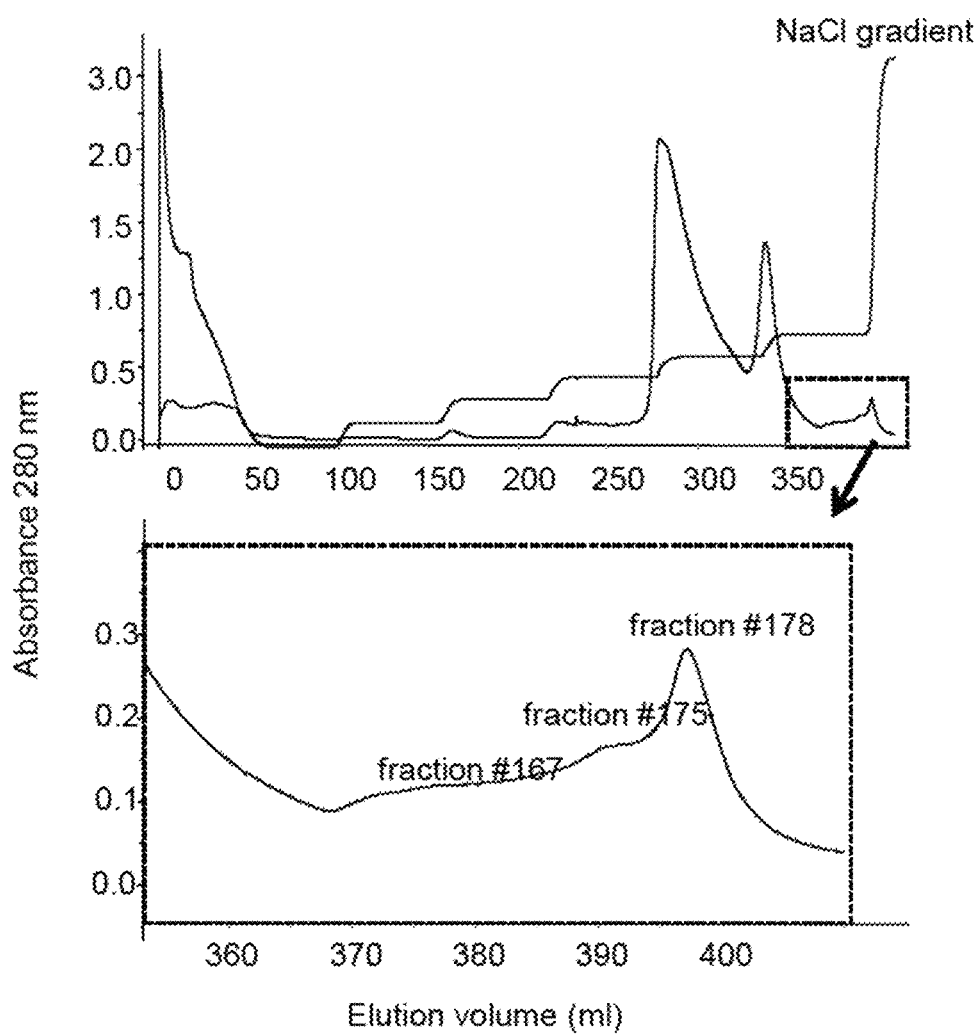

FIG. 2: FPLC profile for elution of the proteins of milk clarified on Heparin Sepharose HR26/16 column, using a discontinuous NaCl gradient with 50 mM increases. On the x-axis: elution volume; on the y-axis: absorbance at 280 nm.

Figure 3:
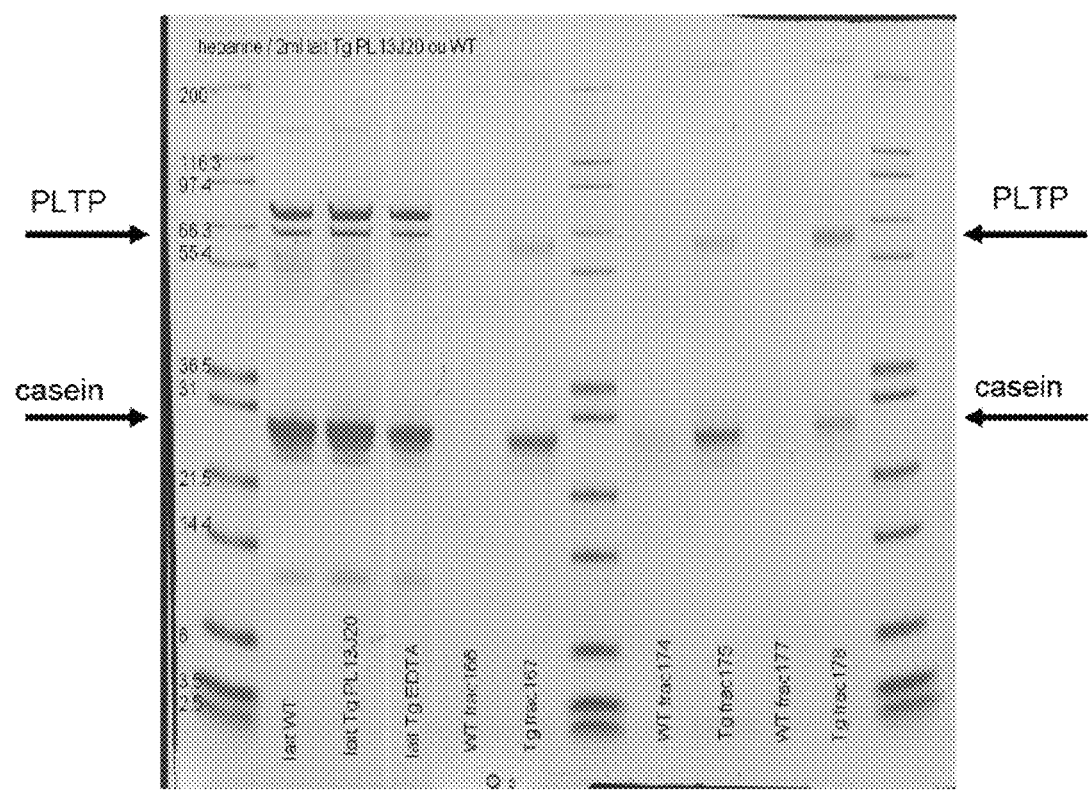

FIG. 3: Polyacrylamide gradient gel electrophoresis under denaturing conditions of fractions #167, #175 and #178 eluted on Heparin Sepharose column.

Figure 4:
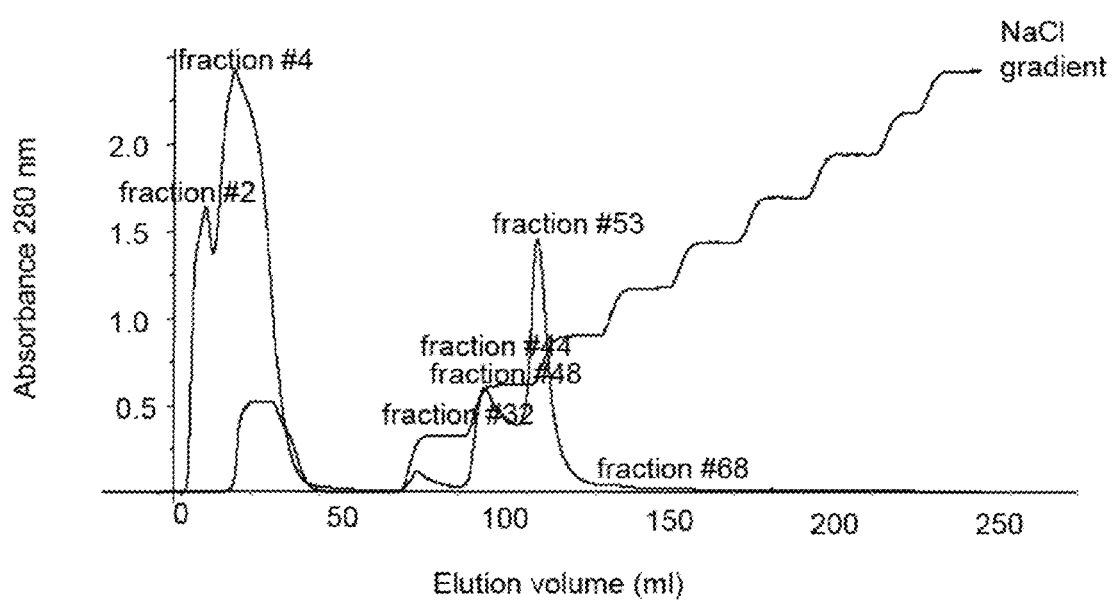

FIG. 4: FPLC profile for elution of the proteins of milk clarified on Heparin Sepharose HR26/16 column, using a discontinuous NaCl gradient with 100 mM increases. On the x-axis: elution volume in milliliters; on the y-axis: absorbance at 280 nm.

Figure 5:
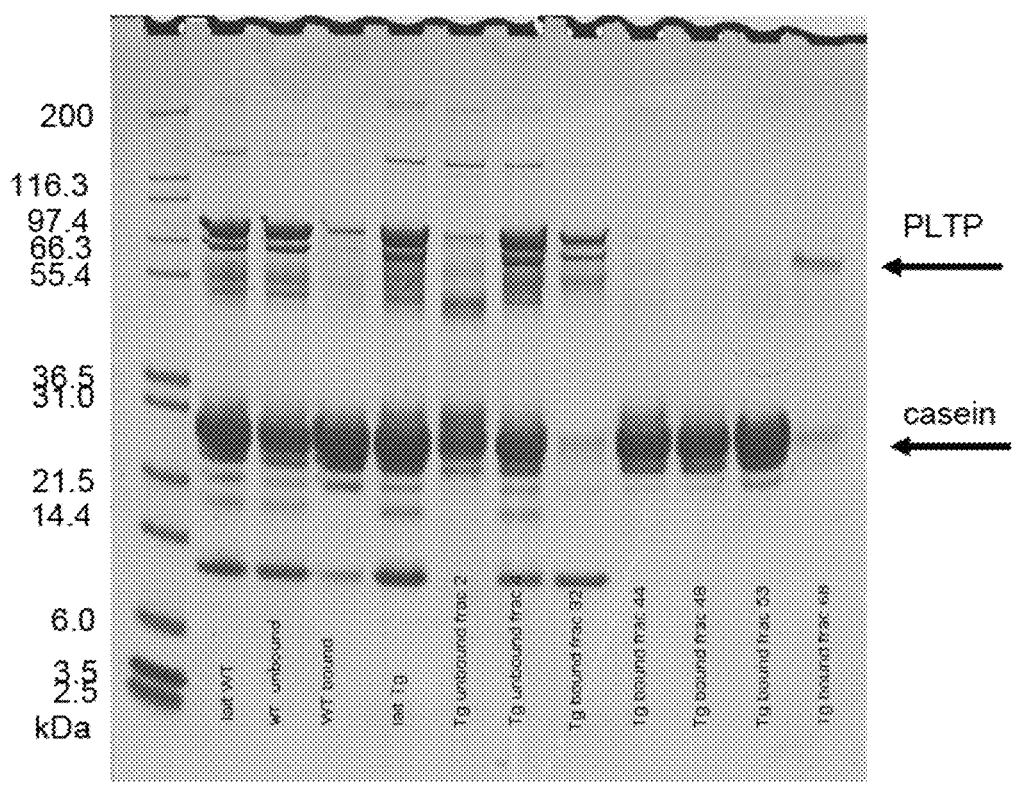

FIG. 5: Polyacrylamide gradient gel electrophoresis under denaturing conditions of fraction #68 eluted on Heparin Sepharose column and having a high phospholipid transfer specific activity. "unbound": unbound fractions; "bound": bound fractions.

Figure 6:
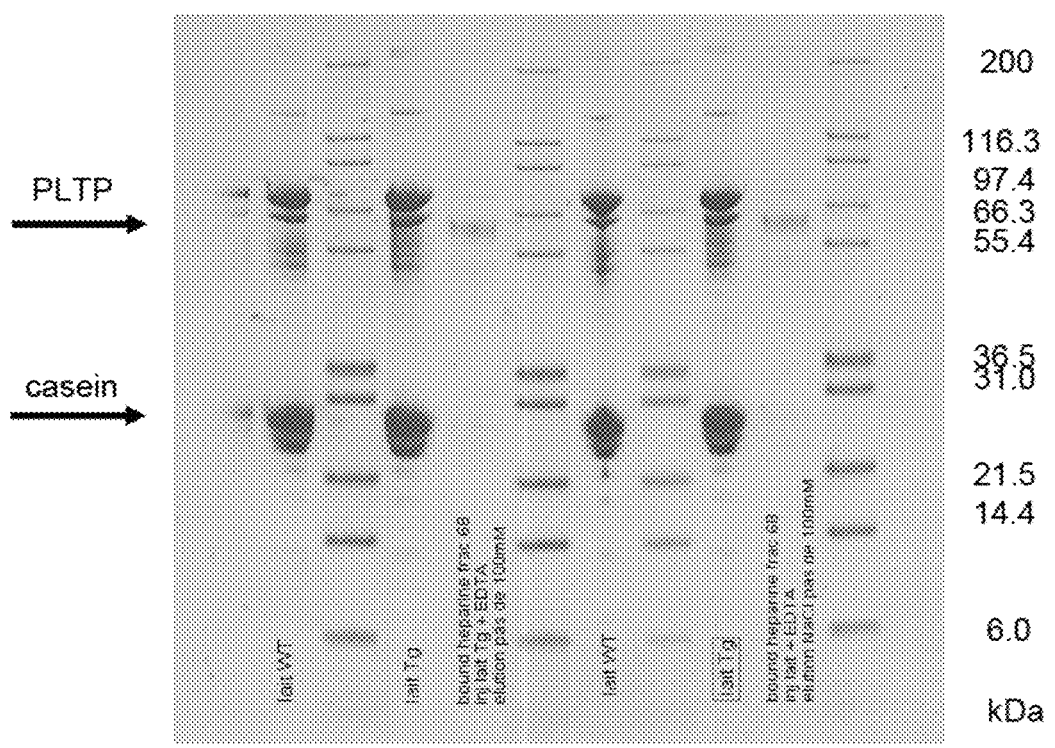

FIG. 6: Second electrophoresis run (same as FIG. 5 with a shorter time for staining with Commassie blue). "bound": bound fractions.

Figure 7:
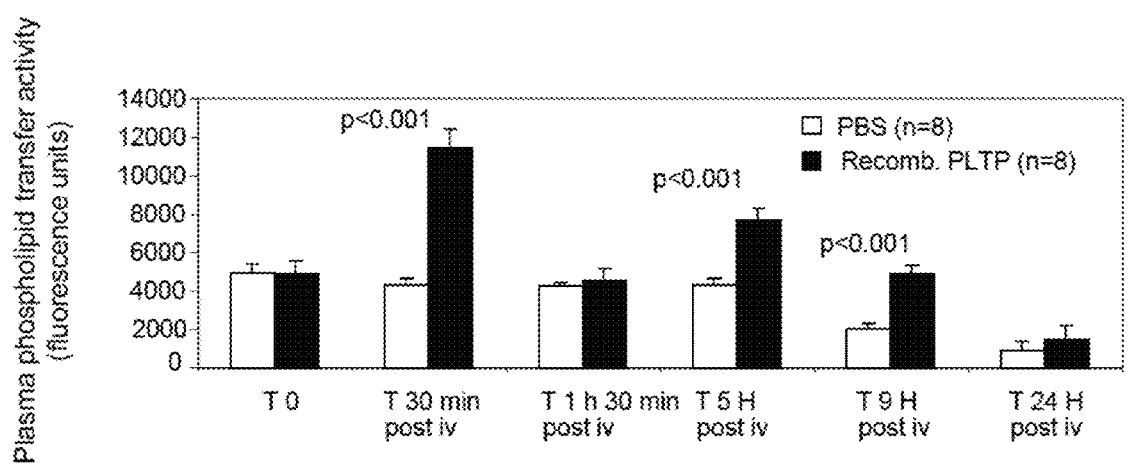

FIG. 7: Phospholipid transfer activity in plasma from PLTP-KO mice injected either with the purified PLTP fraction (black bars), or with an identical volume of PBS buffer (white bars). On the x-axis: the different sampling times; on the y-axis: phospholipid transfer activity (in fluorescence units).

Figure 8:
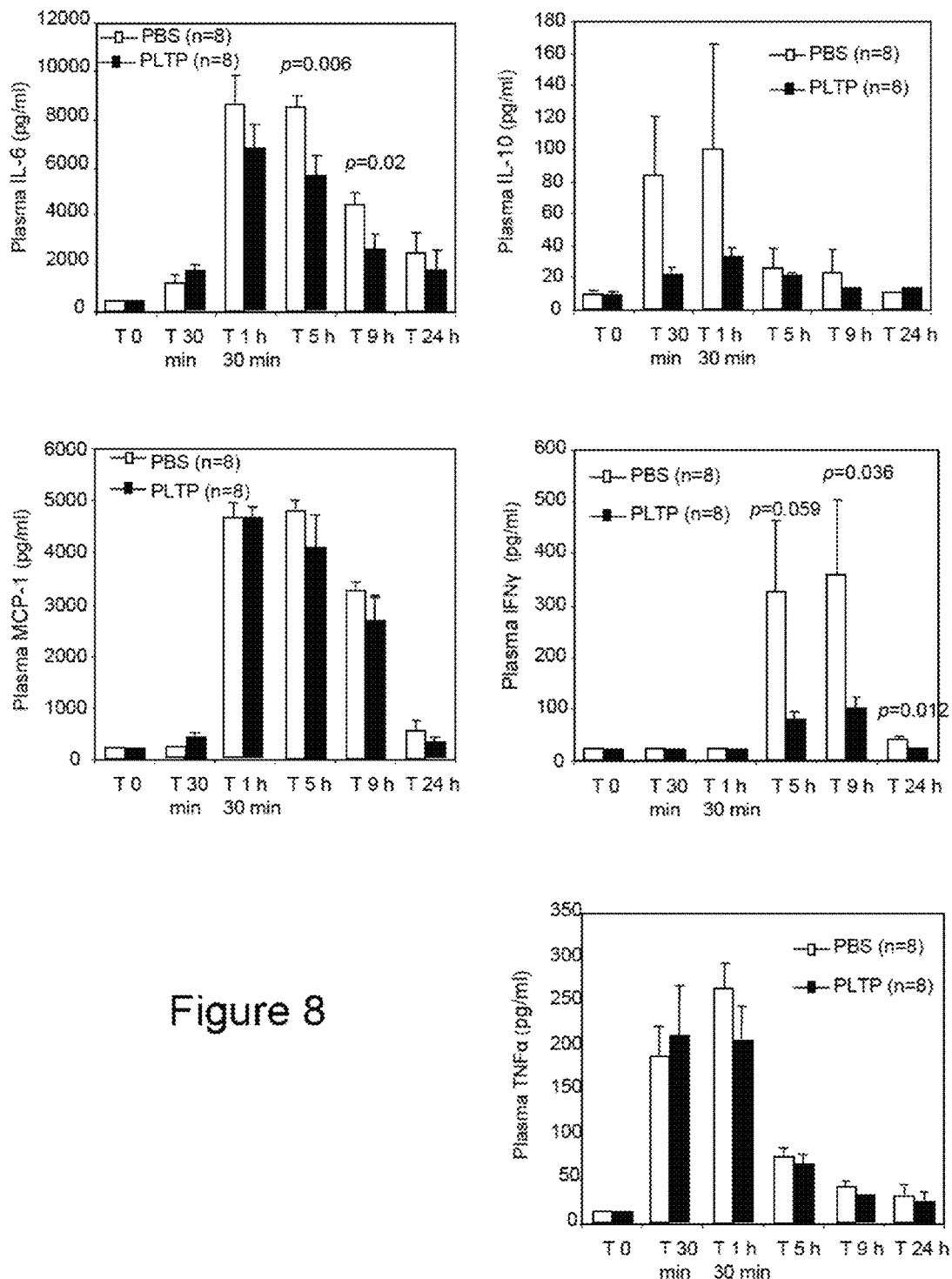

FIG. 8: Plasma concentrations of cytokines after injection of LPS, in animals having received recombinant PLTP (black bars), or PBS buffer (white bars).

Figure 9:
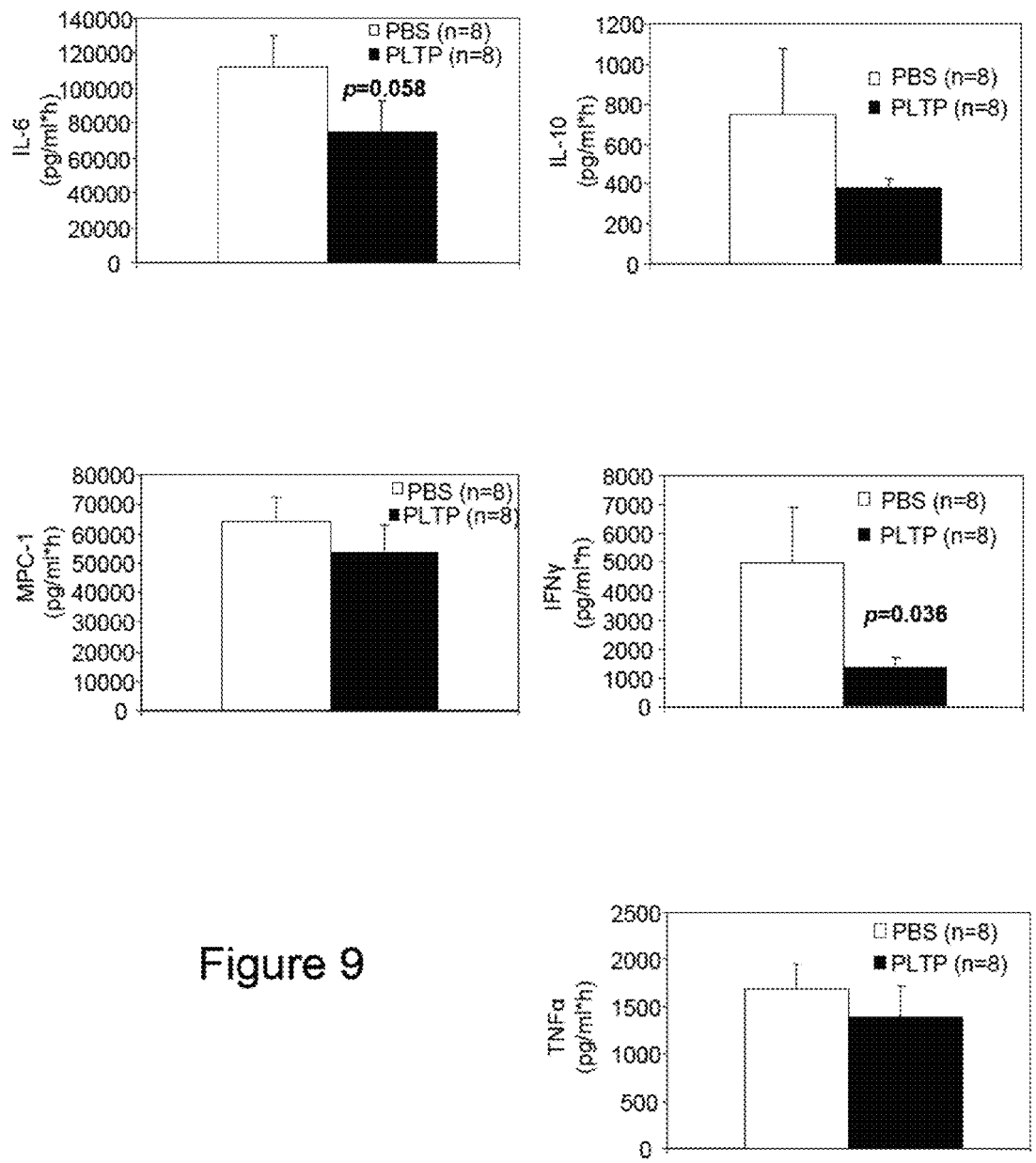

FIG. 9: Area under the curve for the cytokine concentrations measured over a period of 24 hours and expressed in pg/ml of plasma×hour.

Figure 10:
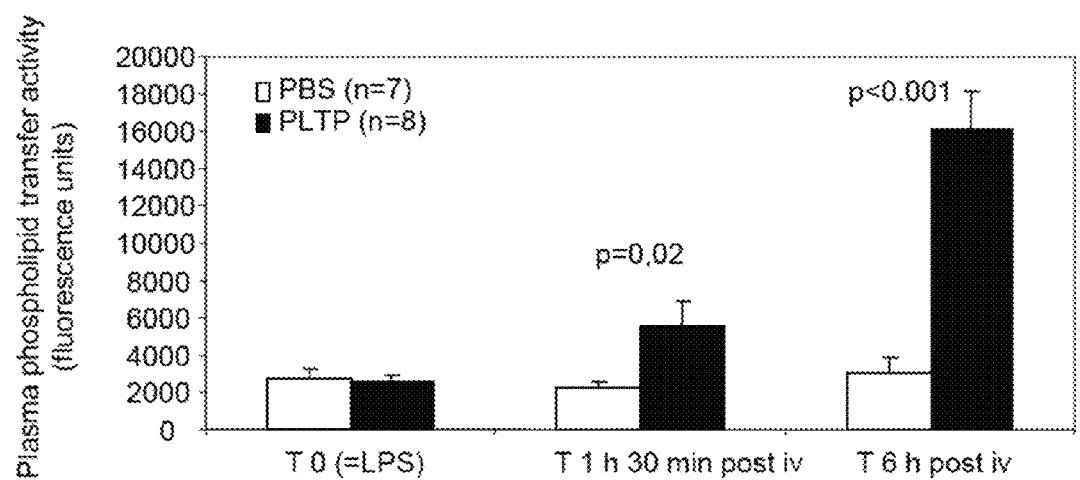

FIG. 10: Phospholipid transfer activity of the plasma of PLTP-KO mice having received 15 mg/kg of LPS, and injected either with the purified PLTP fraction (black bars), or with an identical volume of PBS buffer (white bars).

Figure 11:
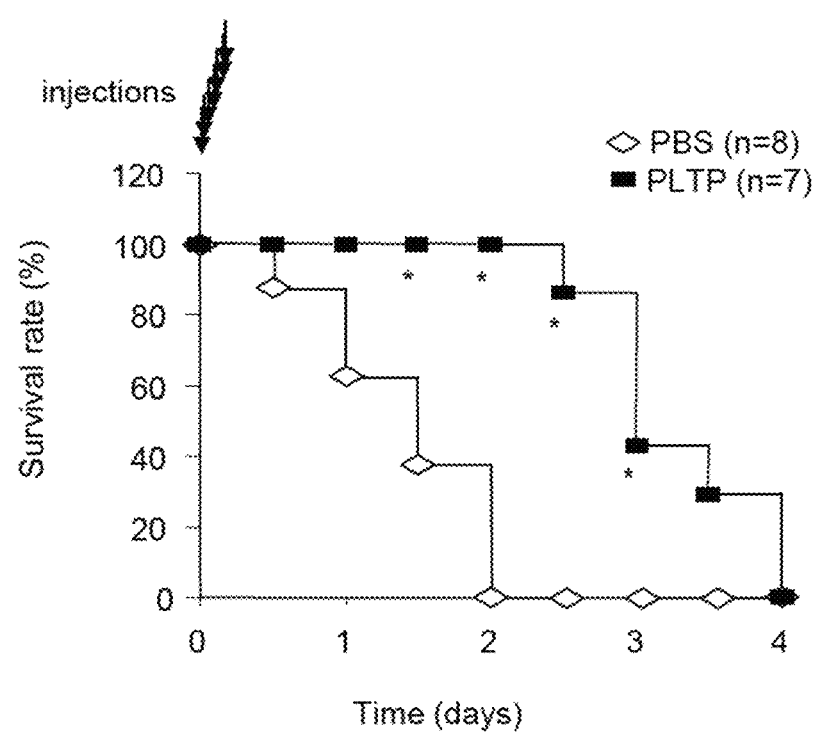

FIG. 11: Kaplan-Meier curves showing the mortality of PLTP-KO mice which have received a single dose of LPS (15 mg/kg, i.p.). Arrows: several intravenous injections (caudal vein) of buffer (PBS) or of recombinant PLTP (PLTP) at the times 15 min, 1 h, 2 h, 3 h, 4 h, 5 h and 7 h post LPS.

Figure 12:
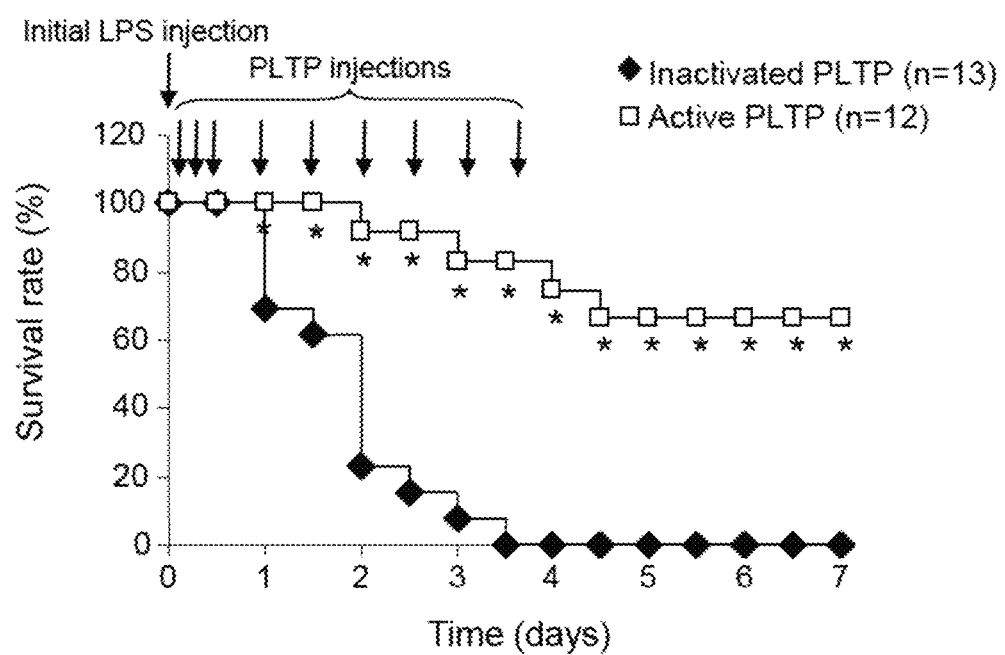

FIG. 12: Kaplan-Meier curves showing the mortality of PLTP-KO mice which have received a single dose of LPS (25 mg/kg, i.p.). Arrows: a single injection of LPS and then several intravenous injections (caudal vein) of active recombinant PLTP (active PLTP) or inactivated recombinant PLTP (inactivated PLTP) at the times 1 h, 5 h, 10 h, 24 h, 32 h, 48 h, 56 h, 72 h and 80 h post LPS.

Figure 13:
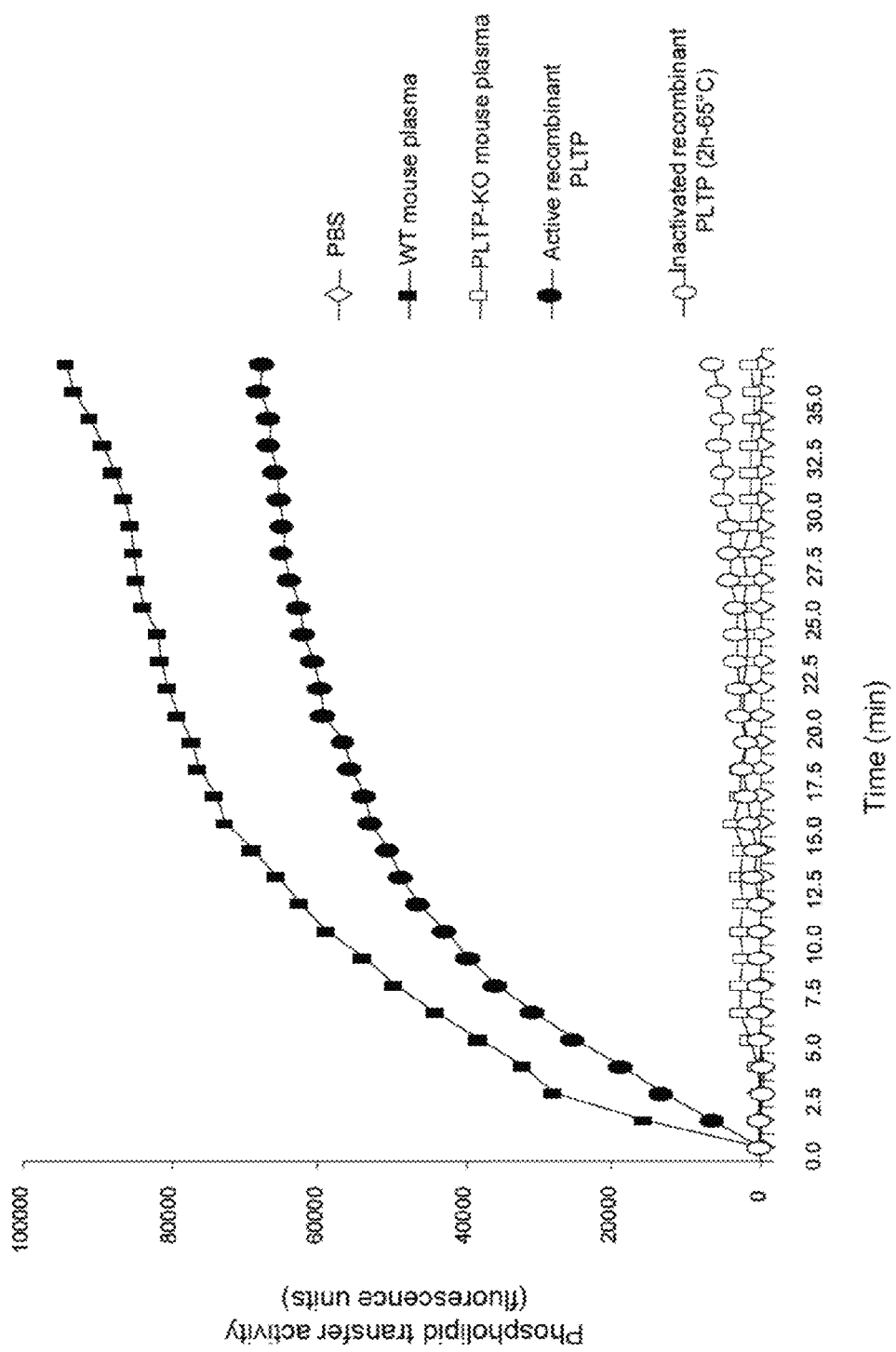

FIG. 13: Comparison of the phospholipid transfer activities of active recombinant PLTP, of inactivated recombinant PLTP (2 h, 65° C.), of a wild-type mouse plasma (WT), of a PLTP-KO mouse plasma, and of a PBS buffer. On the x-axis: time in minutes; on the y-axis: phospholipid transfer activity (in fluorescence units).

EXAMPLE 1: CONSTRUCTION OF A TRANSGENESIS VECTOR CONTAINING THE SEQUENCE ENCODING HUMAN PLTP

Cloning of PLTP cDNA into an Intermediate Vector

A backtranslated synthetic cDNA sequence encoding the human PLTP precursor (UniProtKB/Swiss-Prot P55058), bordered, at the 5' position, by a consensus Kozak sequence and by a unique MluI restriction site and, at the 3' position, by two stop codons and by an NheI restriction site, was synthesized and cloned into an intermediate vector, derived from the plasmid pBluescript, containing the ampicillin resistance gene as well as the Col E1 bacterial replication origin.

Transgenesis Vector

The transgenesis vector used for the cloning is derived from the plasmid pPolyIII, having an ampicillin resistance gene as well as the Col E1 bacterial replication origin. This transgenesis vector contains an expression cassette comprising: a dimer of the 5'HS4 insulator sequence of the chicken beta-globin gene (Genbank U78775) (RECILLAS-TARGA et al., Proc. Natl. Acad. Sci., 10: 6883-6888, 2002) upstream of the 6.3 kbp rabbit WAP promoter (whey acidic protein; Genbank X52564) (RIVAL-GERVIER et al., Transgenic Res., 6: 723-730, 2003), the second intron of the rabbit beta-globin gene (Genbank V00882) containing a transcription enhancer; a second transcription enhancer (SUR 1.2.3) containing the 5'UTR sequence of the SV40 early genes, fused with the R region and the start of the HTLV-1 U5 region (ATTAL et al., FEBS Lett., 392, 220-224, 1996); a third transcription enhancer (Igµ2), derived from the mu region of the mouse IgG heavy chain (Genbank J00440) (GILLIES et al., Cell 33, 717-728, 1983) and the transcription terminator of the human growth hormone (Genbank M13438). This cassette contains an MluI site and an NheI site located between the second and third transcription enhancer; it is flanked on either side by NotI sites allowing the excision of sequences of the plasmid pPolyIII.

The DNA insert encoding PLTP, recovered by MluI/NheI digestion from the intermediate vector, was inserted between the MluI and NheI sites of the expression cassette.

The resulting transgenesis vector contains an insert which consists, in its 5' to 3' orientation, of i) the dimer of the 5'HS4 insulator sequence of the chicken beta-globin gene, ii) the 6.3 kbp rabbit WAP promoter (whey acidic protein), iii) the intron containing the first transcription enhancer, iv) the second transcription enhancer, v) the human PLTP cDNA, yl) the third transcription enhancer, and vii) the transcription terminator.

As above, the colonies containing the recombinant vector are selected on the basis of their ampicillin resistance, and then the presence of the insert is checked by analysis of the restriction fragments, and then by sequencing.

EXAMPLE 2: PRODUCTION OF TRANSGENIC RABBITS EXPRESSING THE HUMAN PLTP IN THEIR MAMMARY GLANDS

The transgenic rabbits were obtained by the conventional microinjection technique (BRINSTER et al., Proc. Natl. Acad. Sci., 82: 4438-4442, 1985).

Preparation of the Inserts for Transgenesis

The transgenesis vector containing the sequence encoding recombinant PLTP was digested by the restriction enzyme NotI and the insert containing the transgene was isolated on agarose gel and then purified on ElutipD (Schleicher-Schuell, Ecquevilly, France) in accordance with the manufacturer's instructions, precipitated with ethanol and then taken up in a buffer containing 10 mM Tris-HCl, 0.1 mM EDTA, pH 7.4.

Preparation of the Donor and Recipient Rabbits

Embryo-donating New Zealand rabbits, aged 16-30 weeks, are treated by the subcutaneous route for 3 days with porcine FSH (Follicle Stimulating Hormone) in order to stimulate follicle development. On the third day, the rabbits receive an intravenous injection of hCG hormone (human Choroidic Hormone), and then the females are mated.

The recipient rabbits are aged 18-20 weeks. A synchronized pseudogestation is induced either by keeping the females for one week in a long day cycle (16 h of light) before they are mated with the vasectomized males, or by a hormone treatment (FSH/LH superovulation).

Microinjection of Embryos Collected and Implantation

On the 4th day, 18-19 h after mating, the embryos are collected from the donor rabbits in order to carry out the microinjection of DNA: the microinjection of DNA is carried out immediately after the collections (15-25 h after mating). The embryos at the one-cell stage are placed in a microdrop of medium under an inverted microscope equipped with Normarsky lenses and with micromanipulators. Individual embryos are positioned and secured using a pipette. The transgene, diluted at a concentration which may vary from 1 ng/µl to 6 ng/µl, in buffer containing 10 mM Tris-HCl, 0.1 mM EDTA, pH 7.4, is preferably microinjected into the male pronucleus of the embryo with the aid of a pipette for injection.

Following the microinjection, the embryos are maintained in culture in vitro for 1 to 5 h (35 to 40° C., 3 to 5% $CO_2$ in air). The quality of the microinjected embryos is then rapidly evaluated under a stereomicroscope. The intact unicellular embryos are then reimplanted under general anesthetic into the lumen of the oviducts of the synchronized recipient rabbits (10 embryos into each oviduct), using a surgical procedure (the oviducts are exteriorized by laparotomy). Parturition may occur naturally 29-31 days after the transfer of embryos. If necessary, it is triggered by injecting ocytocin on the 31st day. The number of young rabbits born compared with the number of embryos reimplanted is of the order of 5 to 20%.

EXAMPLE 3: SELECTION AND CHARACTERIZATION OF THE TRANSGENIC RABBITS

During the embryogenesis process, the microinjected recombinant DNA is randomly integrated into the genome. The newborn rabbits (10 days) are tested for the presence of the transgene by a biopsy of the ear. The genomic DNA is extracted and PCR (Polymerase Chain Reaction) analysis is carried out using primers specific for the recombinant insert.

The rabbits for which the transgene was detected are called "Founders F0".

The founder F0 lines were in addition characterized by i) analysis of the number of copies of transgene integrated into their genome, and ii) determination of the number of sites of integration.

The number of copies of the transgene integrated into the genome of each founder F0 line was determined by quantitative PCR and by Southern blotting. This number varies, depending on the line, from 1 copy per cell to about one hundred copies per cell.

The number of sites of integration was also determined by Southern blotting. This number varies, depending on the line, from 1 to 3 sites per genome.

EXAMPLE 4: EVALUATION OF THE EXPRESSION OF HUMAN RECOMBINANT PLTP IN THE MILK OF THE TRANSGENIC RABBITS

The phospholipid transfer activity in the milk of F0 transgenic rabbits of Example 3 was evaluated.

For that, the phospholipid transfer activity by PLTP was measured in the milk samples using the commercial kit from Roar Biomedical Inc. (New York, N.Y., USA) according to the recommendations of the manufacturer. A fluorescent phospholipid, in this case phosphatidylcholine, is present in an auto-extinction state when it is combined with a liposome-type donor substrate. The phospholipid transfer activity of PLTP is determined by increasing the fluorescence intensity when the fluorescent phospholipid is transferred to an acceptor lipoprotein substrate, for example of the VLDL type ("very low density lipoprotein"), present in the incubation medium (Masson D. et al. Mol Human Reprod 2003; 9: 457).

FIG. 1 represents the comparison between the phospholipid transfer activity in the milk of non-transgenic rabbits, or WT rabbits (Milk A and Milk B), and the milk of several lines of rabbits transgenic for PLTP, or PLTPTg$_{WAP}$ rabbits (Milk 04, Milk 06 and Milk 13). When no significant phospholipid transfer activity is detected in the milk of WT rabbits, the milk of PLTPTg$_{WAP}$ rabbits show a time-dependent capacity to exchange fluorescent phospholipids between synthetic liposomes and plasma VLDL lipoproteins. Milk 13, which exhibits the highest phospholipid transfer activity, was used for the purification of the protein.

EXAMPLE 5: PRODUCTION OF AN ACTIVE HUMAN PLTP PREPARATION FROM TRANSGENIC RABBIT MILK

1—Precipitation of Caseins at Acidic pH and Room Temperature 1 volume of milk is mixed with 2 volumes of 0.5 mM EDTA, pH 8.0 and 7 volumes of MilliQ water. The EDTA makes it possible to chelate the calcium ions and to break the casein micelles which are capable of retaining part of the PLTP.

The pH is gradually reduced to 4 by adding glacial acetic acid dropwise with stirring, in order to completely precipitate the caseins (whose pH, is 4.6).

2—Clarification of the Whey by Low-Speed Centrifugation and Neutralization of the pH After precipitation of the caseins at acidic pH, centrifugation of the mixture for 10 min at 2000 g and at 4° C.

Collection of the intermediate clarified fraction situated between the lipid supernatant and the protein pellet.

Neutralization with solid Tris in a sufficient quantity for obtaining pH 7.4.

Filtration of the fraction thus collected on a glass fiber filter (Millipore AP2004700). It is a conventional filtration, before injection onto the column. It makes it possible to remove the aggregates and/or particles of large size and to thereby protect the column by avoiding its blockage by these aggregates and/or particles of large size.

3—Extraction/Purification of PLTP by Affinity Chromatography on a Heparin Sepharose Column Injection of the clarified and filtered protein fraction, at room temperature, onto a Heparin Sepharose 6 Fast Flow column (240×16 mm ID) equilibrated beforehand with a 20 mM Tris buffer, pH 7.4.

Rate of injection: 1 ml/min with a peristaltic pump.

Rinsing of the column overnight with a 20 mM Tris buffer, pH 7.4.

Connecting of the loaded column to an Akta FPLC system.

Programming of a discontinuous gradient of the 20 mM Tris buffer, pH 7.4 to the 20 mM Tris/1 M NaCl buffer, pH 7.4 (with increases of 50 or 100 mM NaCl).

Dialysis of the fraction against a 150 mmol PBS/1 NaCl buffer, pH 7.4.

The phospholipid transfer activity is measured in each of the fractions (according to the same protocol as in Example 4), and compared with the values for BCA protein assay (assay with a commercial Bicinchoninic Acid Assay kit, Interchim, Montluçon, France).

Results

The results of an extraction carried out using a discontinuous NaCl gradient with 50 mM increases are illustrated by FIGS. 2 and 3.

As shown in FIG. 2, the proteins of the skimmed fraction of milk are eluted from the heparin column in several successive peaks according to the discontinuous NaCl gradient. Several discrete peaks (fractions #167, #175 and #178) are eluted at the highest NaCl concentrations (greater than 250 mM).

The results of the measurement of phospholipid transfer activity are summarized in Table I below.

TABLE I

|  | [prot] g/l | Activity | Specific activity (SA) | SA fraction/SA milk Tg ratio |
|---|---|---|---|---|
| Milk Tg | 92.73 | 17781 | 192 | 1 |
| Fraction #61 | 0.185 | 47 | 254 | 1 |
| Fraction #91 | 0.163 | 379 | 2325 | 12 |
| Fraction #102 | 0.185 | 496 | 2681 | 14 |
| Fraction #119 | 12.398 | 4119 | 332 | 2 |
| Fraction #149 | 5.44 | 5750 | 1057 | 6 |

TABLE I-continued

|  | [prot] g/l | Activity | Specific activity (SA) | SA fraction/SA milk Tg ratio |
|---|---|---|---|---|
| Fraction #167 | 0.215 | 3262 | 15172 | 79 |
| Fraction #175 | 0.21 | 2256 | 10743 | 56 |
| Fraction #178 | 0.469 | 4715 | 10053 | 52 |

The specific activity for phospholipid transfer ("Specific activity (SA)" column of Table I) is highest in fractions #167, #175 and #178, where it is more than 50 times higher than in the starting milk (last column on the right of Table I).

FIG. 3 shows that these fractions consist of 2 predominant proteins having an apparent molecular weight of 30 and 60 kDa respectively. The 30 kDa band corresponds to caseins, found in abundance in the WT and PLTPTg$_{WAP}$ milks. The 60 kDa band is in the region of the MWs conventionally reported for PLTP (between 50 and 70 kDa).

The results of an extraction carried out using a discontinuous NaCl gradient with 100 mM increases are illustrated by FIGS. 4 to 6, and Table II below.

The fraction exhibiting the highest phospholipid transfer specific activity (fraction #68) is eluted at the 300 mM NaCl step (FIG. 4).

This fraction has a specific activity that is 44 times higher than the starting milk (last column on the right of Table II below).

TABLE II

|  | [prot] g/l | Activity | Specific activity (SA) | SA fraction/SA milk Tg ratio |
|---|---|---|---|---|
| Milk WT | 126 | 1193 | 9 | — |
| Milk Tg | 92.73 | 12946 | 140 | 1 |
| Fraction #2 | 2.47 | 3720 | 1506 | 11 |
| Fraction #4 | 14.31 | 6474 | 452 | 3 |
| Fraction #32 | 0.86 | 11 | 13 | 0 |
| Fraction #44 | 2.03 | 4522 | 2228 | 16 |
| Fraction #48 | 1.51 | 4220 | 2795 | 20 |
| Fraction #53 | 3.67 | 5411 | 1474 | 11 |
| Fraction #68 | 0.425 | 2586 | 6085 | 44 |

Electrophoretic analysis under denaturing conditions again shows a major band at 60 kDa corresponding to PLTP, and a more discrete band at 30 kDa corresponding to the caseins (FIG. 5). A second electrophoresis with a less intense staining of the bands shows a single band of 60 kDa for the most active fraction #68 (FIG. 6). These results show that human PLTP is the major constituent of the fraction exhibiting the highest phospholipid transfer specific activity.

EXAMPLE 6: USE OF HUMAN PLTP OBTAINED FROM THE MILK OF TRANSGENIC RABBITS IN THE PREVENTION OF ENDOTOXIN SHOCK IN PLTP-KNOCK-OUT MICE

Previous data (GAUTIER et al., J Biol Chem, 283, 18702-10, 2008) have shown that disabling the endogenous gene for PLTP in mice (homozygous PLTP-KO mice) leads to a reduction in the capacity for neutralizing and detoxifying the LPSs compared to the wild-type WT mice. The mortality after injection of a lethal dose of LPS occurs earlier in the PLTP-KO mice than in the WT mice.

In order to determine if the exogenous supply of recombinant PLTP can increase detoxification of the LPSs and the resistance to endotoxin shock in animals, PLTP-KO mice received, by the intraperitoneal route, a lethal (15 mg/kg) or sublethal (5 mg/kg) injection of LPS at time 0, followed by successive intravenous injections of PBS buffer or of recombinant PLTP (100 microliters of active fraction #68) prepared from the milk of transgenic rabbits as described in Example 5 above. The plasma was then collected by retroorbital puncture in order to assay the circulating concentrations of cytokines (IL-6, IL-10, MCP-1, IFNgamma, TNFalpha), and the phospholipid transfer PLTP activity, according to the protocols described by GAUTIER et al. (2008, cited above). Finally, the mortality rates were recorded over a period of 4 days following the initial injection of LPS.

FIG. 7 illustrates the plasma phospholipid transfer activity in mice, after injection(s) of recombinant PLTP or of PBS buffer. This plasma phospholipid transfer activity is significantly higher 30 minutes after injection of recombinant PLTP compared with mice receiving the PBS buffer. The increase in activity disappears 90 minutes after the first injection of PLTP, but remains significant 60 minutes after the third injection which took place at time 4 hours. Likewise, at time t=9 h, the plasma phospholipid transfer activity is significantly higher in the animals receiving recombinant PLTP compared with the animals receiving the PBS buffer (that is 60 minutes after the last injection of exogenous PLTP at time t=8 h). At time t=24 hours, the animals which received the last injection of recombinant PLTP at time t=8 h no longer exhibit an increase in plasma phospholipid transfer activity compared with the animals which received the PBS buffer.

These results show that the injection of exogenous PLTP in PLTP-KO mice leads to a significant and transient rise in the plasma phospholipid transfer activity with a persistence of the order of 60 minutes.

To study the effects of recombinant PLTP on the production of the cytokines IL-6, IL-10, MCP-1, IFNgamma and TNFalpha, animals having received a single intraperitoneal injection of LPS at sublethal dose (5 mg/kg) then received several intravenous injections (caudal vein) of PBS buffer or of recombinant PLTP, 10 min, 2 h, 4 h, 6 h and 8 h after the administration of the LPSs. Retroorbital blood samples were collected at times T 0, T 30 min, T 1 h 30 min, T 5 h, T 9 h and T 24 h in the animals anesthetized with isoflurane, and the cytokines were assayed.

The results are illustrated by FIGS. 8 and 9.

After injection of the single dose of LPS at 5 mg/kg, the circulating concentrations of cytokines follow a biphasic variation during the 24 hour period studied, with an initial phase of increase, followed by a phase of decrease leading at t=24 h to the background values measured in the PLTP-KO mice at time t=0 (FIG. 8). A significant reduction in the circulating concentrations of IL-6, IL-10 and IFNgamma is observed at various times in the mice receiving recombinant PLTP compared with the mice receiving PBS. The cytokines IL-6, IL-10, MCP-1, IFNγ and TNF show biphasic curves, with significantly lower IL-6 and IFNγ production. The calculation of the area under the curve (AUC) during the 24 hour period studied shows significantly lower values of IL-6 (p=0.058) and of IFNgamma (p=0.036) in mice receiving the recombinant PLTP by the intravenous route than in those which received PBS (FIG. 9).

In order to study the effect of exogenous PLTP on mortality, the intraperitoneal injection of a single lethal dose of LPS at 15 mg/kg was followed by a sequence of intravenous injections of exogenous PLTP at times t=15 min, t=1 h, t=2 h, t=3 h, t=4 h, t=5 h, t=7 h after injection of the LPSs. Retroorbital blood samples were collected in the animals anesthetized at times T 0, T 1 h 30 min and T 6 h after injection of the LPSs, and the plasma phospholipid transfer activity was determined. The length of survival of the animals was noted in parallel.

The results are illustrated in FIGS. 10 and 11.

As shown in FIG. 10, the plasma phospholipid transfer activity is significantly higher 30 minutes after the second injection in the mice receiving recombinant PLTP compared with the mice receiving the PBS buffer. An increase in activity (of the order of 5 times) is observed at time t=6 h, that is 1 hour after the $4^{th}$ injection of recombinant PLTP. Again, these results show that the cumulative injection of exogenous PLTP in the PLTP-KO mice leads to a significant and transient rise in the plasma phospholipid transfer activity with a persistence of at least 60 minutes. The Kaplan-Meier curves (FIG. 11) show the extension of the survival of the animals which received the exogenous recombinant PLTP compared with the animals which received the PBS buffer. The average lengths of survival are 33.6±5.4 h (mean±sem) for the mice which received PBS (n=8) and 77.1±6.2 h (mean±sem) for the mice (n=7) which received the PLTP (p<0.05 against PBS by the Chi2 test).

These results demonstrate the beneficial effect of an exogenous PLTP supply in animals subjected to an endotoxin shock by a single intraperitoneal injection of LPS. Successive injections of PLTP during the first few hours following the injection of LPS significantly reduce the production of inflammatory cytokines and extend survival.

EXAMPLE 7: USE OF ACTIVE OR INACTIVATED HUMAN PLTP OBTAINED FROM THE MILK OF TRANSGENIC RABBITS IN THE PREVENTION OF ENDOTOXIN SHOCK IN PLTP-KNOCK-OUT MICE

In order to confirm the effect of exogenous PLTP on the mortality, observed in Example 6, the intraperitoneal injection of a single lethal dose of LPS (25 mg/kg of body weight) was followed by a sequence of intravenous injections of recombinant PLTP (200 microliters, 2.2 g proteins/l), prepared from the milk of transgenic rabbits as described in Example 5, at times t=1 h, 5 h, 10 h, 24 h, 32 h, 48 h, 56 h, 72 h and 80 h after the injection of LPS.

The survival rate was followed as a function of time, as represented in FIG. 12. The effect of the active recombinant PLTP was compared with that of a PLTP inactivated by heating a preparation of recombinant PLTP, purified according to Example 5, for 2 hours at 65° C. The Kaplan-Meier curves were compared by the Chi2 test. After 4 days, all the mice injected with LPS and then inactivated PLTP died. The injection of active recombinant PLTP makes it possible to very significantly increase (p<0.05 against inactivated PLTP) the survival of the animals. More than 60% of the mice are permanently saved (beyond 7 days). The intravenous injection of active exogenous recombinant PLTP, as opposed to the same PLTP inactivated by heating, therefore increases the survival of the PLTP-KO mice which received an injection of a lethal dose of LPS.

The phospholipid transfer activity of the inactivated PLTP was measured by fluorescence with the aid of a commercial kit (Roar Biomedical Inc.), as in Example 4, and compared with those of a PBS buffer, of active recombinant PLTP, of a wild-type (WT) mouse plasma, and of a PLTP-KO mouse plasma. The results, illustrated by FIG. 13, show that only the WT mouse plasma and the active recombinant PLTP make it possible to detect a phospholipid transfer activity, the inactivated recombinant PLTP, like the PBS buffer and the PLTP-KO mouse plasma, resulting in no significant activity.

These results confirm the beneficial effect of an exogenous PLTP supply in animals subjected to an endotoxin shock by single intraperitoneal injection of LPS. Successive injections of PLTP during the first few hours following the injection of LPS significantly extend survival.

The invention claimed is:

1. A method of producing an active recombinant human plasma phospholipid transfer protein (PLTP) preparation, said method comprising
    (i) harvesting milk produced by a transgenic rabbit secreting active human PLTP in its milk,
    (ii) precipitating casein in the harvested milk in the presence of EDTA at acidic pH of less than or equal to 4.6,
    (iii) clarifying the product obtained in (ii) and recovering the whey, and
    (iv) extracting the PLTP from the whey to form the PLTP preparation;
    wherein the PLTP preparation has a phospholipid transfer activity at least 50 times higher than in untreated milk produced by a transgenic animal that secreted active human PLTP in its milk.

2. The method as claimed in claim 1, wherein the extraction of the PLTP from the whey is carried out by affinity chromatography on heparin.

3. The method of claim 2, wherein the PLTP is extracted with a salt concentration of greater than 250 mM.

4. The method of claim 1, wherein ultracentrifugation is used to clarify the product in step (iii).

* * * * *